United States Patent [19]

Yasunami et al.

[11] Patent Number: 4,656,194

[45] Date of Patent: Apr. 7, 1987

[54] AZULENE DERIVATIVES AND THEIR USE AS HYPOCHOLESTEROLEMICS

[75] Inventors: Masabumi Yasunami; Kahei Takase, both of Sendai; Akira Shinji; Toru Mimura, both of Kawasaki; Kunio Torii, Tokyo; Takaaki Kobayashi, Yokohama; Masaru Okutsu, Yamato; Takashi Meguro, Zushi, all of Japan

[73] Assignee: Ajinomoto Co., Inc., Tokyo, Japan

[21] Appl. No.: 785,713

[22] Filed: Oct. 9, 1985

[30] Foreign Application Priority Data

Oct. 17, 1984 [JP] Japan .................................. 59-218123

[51] Int. Cl.4 ...................... A61K 31/11; C07C 13/52; C07C 47/40
[52] U.S. Cl. ..................................... 514/693; 568/445
[58] Field of Search .......................... 568/445; 514/693

[56] References Cited

FOREIGN PATENT DOCUMENTS 1059447 6/1959 Fed. Rep. of Germany ...... 568/445

OTHER PUBLICATIONS

Plattner et al, Chem. & Ind., No. 39, (1954), 1202-1203.

Primary Examiner—Bernard Helfin
Attorney, Agent, or Firm—Oblon, Fisher, Spivak, McClelland & Maier

[57] ABSTRACT

An azulene derivative capable of exerting a hypocholesterolemic effect on a mammal which is represented by the formula

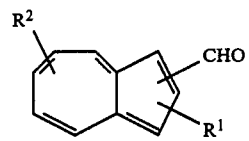

wherein $R^1$ and $R^2$ are the same or different and are selected from the group consisting of hydrogen, $C_1$-$C_{12}$ alkyl groups and $C_2$-$C_{12}$ alkenyl groups.

8 Claims, No Drawings

AZULENE DERIVATIVES AND THEIR USE AS HYPOCHOLESTEROLEMICS

BACKGROUND OF THE INVENTION

1. Field of the Invention

This invention relates to azulene derivatives and to compositions containing the same.

2. Description of the Related Art

The azulene derivatives of this invention have not been reported in the literature, nor is there any literature suggesting the hypocholesterolemic effect of a compound having the azulene nucleus.

Hyperlipemia, especially hypercholesterolemia, is known to be a cause of arteriosclerosis and related diseases, and new compounds which exhibit hypocholesterolemic activity are of interest.

SUMMARY OF THE INVENTION

Accordingly, it is an object of this invention to provide a new class of compounds which exhibit a hypocholesterolemic effect.

It is another object of this invention to provide hypocholesterolemic compositions containing as an active ingredient a new class of hypocholesterolemic compounds.

According to the present invention, the above and other objects are obtained by providing azulene derivatives represented by the following formula

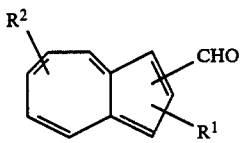

where $R^1$ and $R^2$ are the same or different and are selected from the group consisting of hydrogen, $C_1-C_{12}$ alkyl groups (e.g., methyl, ethyl, isopropyl, t-butyl and n-pentyl), and $C_2-C_{12}$ alkenyl groups (e.g., vinyl, allyl, isopropenyl and isopentenyl). It has been found that these compounds show no adverse side effects and can be used as an active ingredient in hypocholesterolemic compositions.

DETAILED DESCRIPTION OF THE PREFERRED EMBODIMENTS

According to the invention, $R^1$ and —CHO groups may be attached to any position on the five-membered ring (1-, 2- and 3-positions), and $R^2$ may be attached to any position on the seven-membered ring (4, 5, 6, 7 and 8 positions).

In a preferred embodiment, the azulene derivatives have $R^1$, $R^2$, and CHO substituents positioned on the azulene ring as follows:

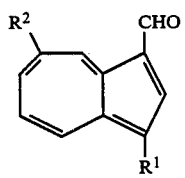

In this preferred embodiment, $R^2$ is preferably $C_1-C_{12}$ alkyl and $R^1$ is $C_1-C_{12}$ alkyl or $C_1-C_{12}$ alkenyl.

In a particularly preferred embodiment $R^2$ is isopropyl and $R^1$ is $C_1-C_{12}$ alkyl.

The azulene derivatives of this invention can be prepared, for example, by the reaction:

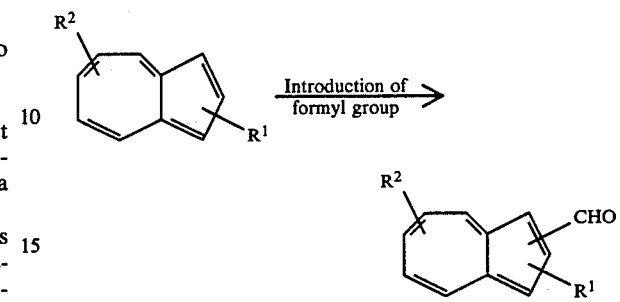

(wherein $R^1$ and $R^2$ are as defined above). The introduction of a formyl group onto the five-membered ring may be accomplished by the Vilsmeier reaction (for example, reaction with dimethylformamide and phosphorus oxychloride). See, for example, H. O. House in Modern Synthetic Reactions, W. A. Benjamin, Inc. Reading, Mass. p. 769 (1972). The products can be isolated from the reaction mixture by removal of the solvent under reduced pressure, followed by purification by column chromatography on alumina.

The resulting azulene derivatives are effective in preventing and treating hyperlipemia of humans and mammals, and may be administered orally in tablet, capsule or elixir form, or parenterally in the form of a solution or a suspension.

The total daily dose of the azulene derivative is in the range from 1 mg to 2000 mg (0.2 to 500 mg × several times a day). The optimum dose may vary with the severity of disease, weight of patient and other factors known to those skilled in the art.

When a hypocholesterolemic composition is formulated from an azulene derivative, a physiologically acceptable salt of the azulene derivative, or a mixture thereof (about 0.2 to 500 mg), the composition is shaped, together with a physiologically acceptable vehicle, carrier, excipient, binder, antiblocking agent, preservative, stabilizer, flavoring and/or other additive, into unit dosage form.

Typical examples of additives that can be used in tablets and capsules are binders such as tragacanth gum, gum arabic, corn starch and gelatin; excipients such as microcrystallline cellulose; swelling agents such as corn starch, pre-gelatinized starch and alginic acid; lubricants such as magnesium stearate; sweeteners such as sucrose, lactose and aspartame; and perfumes such as peppermint. Other additives include edible oil as a liquid carrier (in capsules); and shellac, sugar and a combination thereof (tablet coating).

Parenteral injections may employ, as a vehicle to dissolve or suspend the active ingredient, water, natural vegetable oils such as sesame oil, coconut oil, peanut oil and cottonseed oil, and synthetic oils such as ethyl oleate, and may also contain buffering agents, preservatives and anti-oxidants as required.

The invention now being generally described, the same will be better understood by refenence to certain specific examples which are included herein for purposes of illustration only and are not intended to be limiting of the invention or any embodiment thereof, unless specified.

EXAMPLE 1

Preparation of 3-ethyl-7-isopropylazulene-1-aldehyde

An ice-cooled solution (15 ml) of 2.32 g of phosphorus oxychloride in dimethylformamide was added dropwise to a solution (15 ml) of 1.5 g 1-ethyl-5-isopropylazulene in dimethylformamide.

Stirring under ice cooling was continued for seven hours, and the reaction mixture was poured into about 200 ml of ice water for decomposition. After adjusting the pH to 10 with a caustic soda solution, the mixture was thoroughly extracted with benzene. Distilling off the solvent from the benzene extract gave 1.6 g of crude 3-ethyl-7-isopropylazulene-1-aldehyde (yield: 95%), which was recrystallized from n-hexane, affording the pure product melting at 60° to 62° C.

EXAMPLE 2

Preparation of 3-n-butyl-7-isopropylazulene-1-aldehyde

The title compound was prepared in an analogous manner to Example 1 starting from 1-n-butyl-5-isopropylazulene.

EXAMPLE 3

Preparation of 3-n-octyl-7-isopropylazulene-1-aldehyde

The title compound was prepared in an analogous manner to Example 1, starting with 1-n-octyl-5-isopropylazulene aldehyde.

Table 1 summarizes the properties of the above exemplary compounds.

EXAMPLE 4

Pharmacological Test (1) Hypocholesterolemic Effect Upon Mice

ICR male mice (21-days-old) were fed a commercial diet for two days, and then supplied with an experimental diet containing 1% cholesterol for seven days. The composition of the experimental diet used in this test is as follows:

| Components | Percentage |
| --- | --- |
| Sucrose | 59.79 |
| Casein | 20.0 |
| Powdered filter paper | 4.0 |
| Minerals complex* | 4.0 |
| Vitamins complex* | 1.0 |
| Choline chloride | 0.2 |
| Cholesterol | 1.0 |
| Palm oil | 5.0 |
| Soybean oil | 5.0 |
| Vitamin E | 0.01 |

*Products of Oriental Yeast Co., Ltd. (Harper's formulation)

TABLE 1

Structure and Nature of Azulene Derivatives

| Example No | Structural Formula | Molecular Formula | Crystalline form | M.P. | IR (IN CHCl₃) | ppm | H¹—NMR [60 MHz in CDCl₃] (Proton Splitting coupling reversion, number, pattern, constant, sion) |
| --- | --- | --- | --- | --- | --- | --- | --- |
| 1 | (7-isopropyl, 3-CH₂CH₃, 1-CHO azulene) | $C_{16}H_{18}O$ | dark purple squama crystal | 60–62° C. | 2970(m), 1620(s), 1538(w), 1440(s), 1402(s), 1380(m), 1300(m), 1160(m), 910(w), 890(w), 818(w), 705(s) | 1.35, 1.38, 2.95, 3.18, 7.30, 7.65, 7.97, 8.20, 9.45, 10.23 | (t, J=7.0, CH₂CH₃); (d, J=7.0, isoPrCH₃); (q, J=7.0, CH₂CH₃); (sept, J=7.0, isoPrCH); (dd, J=10.0, 10.0, H—5); (dm, J=10.0, H—4); (s, H—2); (dd, J=10.0, 2.0, H—6); (d, J=2.0, H—8); (s, CHO) |
| 2 | (7-isopropyl, 3-(CH₂)₃CH₃, 1-CHO azulene) | $C_{18}H_{22}O$ | purple oil | oil | 1648 | 0.92, 1.17–2.00, 1.37, 2.90, 3.15, 7.27, 7.57, 7.93, 8.13, 9.40 | (3H, t, J=6.0, CH₃); (4H, m, CH₂); (6H, d, J=7.0, isoPrCH₃); (2H, t, J=6.0, ≡C—CH₂); (1H, sept, J=7.0, isoPrCH); (1H, dd, J=10.0, 10.0, H—5); (1H, ddd, J=10.0, 2.0, 1.0, H—6); (1H, s, H—2); (1H, dd, J=10.0, 1.0, H—4); (1H, d, J=2.0, H—8), 10.15(1H, s, CHO) |
| 3 | (7-isopropyl, 3-(CH₂)₇CH₃, 1-CHO azulene) | $C_{22}H_{30}O$ | purple oil | oil | 1645 | 0.83, 1.03–1.92, 1.37, 2.90, 3.18, 7.25, 7.42, 7.92, 8.15, 9.42 | (3H, t, J=6.0, CH₃); (12H, m, CH₂); (6H, d, J=7.0, isoPrCH₃); (2H, t, J=6.0, ≡C—CH₂); (1H, sept, J=7.0, isoPrCH); (1H, dd, J=9.5, 9.5, 9.5, H—5); (1H, ddd, J=9.5, 2.0, 1.0, H—6); (1H, s, H—2); (1H, dd, J=9.5, 1.0, H—4); (1H, d, J=2.0, H—8), 10.17(1H, s, CHO) |

The substances listed in Table 2-1 were orally administered forcibly to each mouse by means of a gastric catheter on the sixth and seventh days from the start of feeding on the experimental diet.

Test animals were grouped prior to the first administration on the sixth day (each group consisting of 10 rats, with each member weighing 21.2±1.2 g on average). After the second administration on the seventh day, the animals were forced to fast for 16 hours, blood samples were taken under etherization, the plasma was obtained by the usual method, and the total cholesterol was determined by an Hitachi Model 706D Automatic Analyzer.

The growth data and cholesterol measurements are summarized in Table 2-2 (the enzymic method was used for cholesterol measurement).

The total cholesterol was substantially reduced by administration of the azulene derivatives of this invention, while no significant difference was observed in the gain of body weight, nor any detectable abnormality upon dissection.

(2) Hypocholesterolemic Effect Upon Rats

SD male rats (28-days-old) were used for this test. The animals were housed individually with free access to food and water. Each rat was fed a commercial diet for two days, and then supplied with an experimental feed containing 0.7% cholesterol for seven days. The composition of the experimental feed used in this test is as follows:

| Components | Percentage |
| --- | --- |
| Sucrose | 59.79 |
| Casein | 20.0 |
| Powdered filter paper | 4.0 |
| Minerals complex* | 4.0 |
| Vitamins complex* | 1.0 |
| Choline chloride | 0.2 |
| Cholesterol | 0.7 |
| Cholic acid | 0.3 |
| Palm oil | 5.0 |
| Soybean oil | 5.0 |
| Vitamin E | 0.01 |

*Products of Oriental Yeast Co., Ltd. (Harper's formulation)

TABLE 2-1

| | Composition of Material Administered | Azulene Deriv. Administration Per 1 kg Body Weight | Administration Volume Per 10 g Body Weight |
| --- | --- | --- | --- |
| Group 1 | 0.25% Carboxymethyl cellulose sodium | control | 0.5 ml |
| Group 2 | 0.25% Carboxymethyl cellulose sodium 8 mg/ml Azulene Derivative (Ex. 1) | 400 mg/Kg | 0.5 ml |

*For administration, the azulene derivatives in crystalline form are powdered in a glass-mortar and mixed with 0.25% CMC solution. After mixture, it is treated by supersonication and suspended well. Before administration, it is stirred again to be administered.

TABLE 2-2

| | Body Weight Before Administration (g/mouse) | Body Weight After Administration (g/mouse) | Total Cholesterol in the Serum (mg/dl) |
| --- | --- | --- | --- |
| Group 1 (Control) | 20.8 ± 1.2 | 22.2 ± 0.8 | 426 ± 115 |
| Group 2 Ex. 1 400 mg/Kg | 21.3 ± 1.4 | 21.3 ± 1.8 | 95 ± 24 |
| Group 3 Ex. 2 400 mg/Kg | 21.8 ± 1.2 | 22.8 ± 1.4 | 430 ± 108 |
| Group 4 Ex. 3 400 mg/Kg | 20.9 ± 1.1 | 21.9 ± 1.3 | 375 ± 85 |

The substances listed in Table 3-1 were orally administered forcibly to each rat by means of a gastric cathether on the sixth and seventh days from the start of feeding on the experimental diet.

Test animals were grouped prior to the first administration on the sixth day (each group consisting of 6 rats, with each member weighing 122.4±6.0 g on average). After the second administration on the seventh day, the animals were forced to fast for 16 hours, and the total sum cholesterol was determined in the same manner as in (1) above. The result is summarized in Table 3-2.

The total cholesterol was markedly reduced with increasing dose of the azulene derivatives of this invention, while no significant difference was observed in the gain of body weight. Fatty livers, which were observed in the control group, were found to have been relieved in the 400 mg/Kg test group. The result is shown in Table 3-2.

TABLE 3-1

| | Composition of Material Administered | Azulene Deriv. Administration Per 1 kg Body Weight | Administration Volume Per 10 g Body Weight |
| --- | --- | --- | --- |
| Group 1 | 0.25% Carboxymethyl Cellulose sodium | Control | 5.0 ml |
| Group 2 | 0.25% Carboxymethyl Cellulose sodium + 1 mg/ml Ex. 1 | 50 gm/Kg | 5.0 ml |
| Group 3 | 0.25% Carboxymethyl Cellulose sodium + 2 mg/ml Ex. 1 | 100 mg/Kg | 5.0 ml |
| Group 4 | 0.25% Carboxymethyl Cellulose sodium + 8 mg/ml Ex. 1 | 400 mg/Kg | 5.0 ml |

TABLE 3-2

| | Body Weight Before Administration (g/mouse) | Body Weight After Administration (g/mouse) | Total Cholesterol in the Serum (mg/dl) |
| --- | --- | --- | --- |
| Group 1 (Control) | 122.5 ± 6.3 | 126.3 ± 6.8 | 302 ± 115 |
| Group 2 Ex. 1 50 mg/Kg | 123.2 ± 7.2 | 125.6 ± 7.9 | 179 ± 48 |
| Group 3 Ex. 1 100 mg/Kg | 122.0 ± 4.7 | 125.5 ± 5.4 | 125 ± 46 |
| Group 4 Ex. 1 400 mg/Kg | 122.0 ± 4.3 | 123.9 ± 5.5 | 110 ± 40 |

EXAMPLE 5

| | |
| --- | --- |
| 3-Ethyl-7-isopropylazulene-1-aldehyde | 25.0 g |
| Sucrose | 74.0 g |
| Magnesium stearate | 1.0 g |

The components listed above were intimately mixed, the mixture was passed through a 60-mesh screen, and the fine powder thus obtained was charged in gelatin capsules (200 mg per piece).

The invention now being fully described, it will be apparent to one of ordinary skill in the art that many changes and modifications can be made thereto without departing from the spirit or scope of the invention as set forth herein.

What is claimed as new and desired to be secured by Letters Patent of the United States is:

1. An azulene derivative represented by the following formula

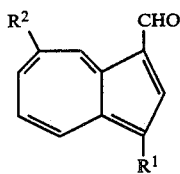

wherein $R^1$ and $R^2$ are the same or different and are each $C_1$-$C_{12}$ alkyl or $C_2$-$C_{12}$ alkenyl.

2. The azulene derivative of claim 1, wherein the alkyl group is methyl, ethyl, isopropyl, t-butyl or n-butyl.

3. The azulene derivative of claim 1, wherein the alkenyl group is vinyl, allyl, isopropenyl or isopentenyl.

4. The azulene derivative of claim 1, which is 3-ethyl-7-isopropylazulene-1-aldehyde.

5. The azulene derivative of claim 1, which is 3-n-butyl-7-isopropylazulene-1-aldehyde.

6. The azulene derivative of claim 1, which is 3-n-octyl-7-isopropylazulene-1-aldehyde.

7. A hypocholesterolemic composition containing an azulene derivative represented by the formula

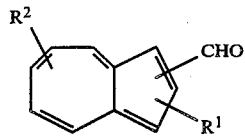

wherein R and $R^2$ are the same or different and are selected from the group consisting of hydrogen, $C_1$-$C_{12}$ alkyl groups and $C_2$-$C_{12}$ alkenyl groups, a physiologically acceptable salt of said derivative, or a mixturer thereof, admixed with a physiologically acceptable vehicle, carrier, excipient or binder, wherein said derivative is contained in said composition in an amount sufficient to exert a hypocholesterolemic effect on a mammal.

8. A method of treating hypercholesterolemia, which comprises administering to a mammal in need of such treatment an amount of a compound of the formula

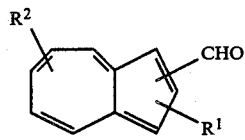

sufficient to exert a hypocholesterolemic effect on said mammal.

* * * * *